United States Patent [19]

Dekeyser et al.

[11] Patent Number: 5,131,940
[45] Date of Patent: Jul. 21, 1992

[54] DIOXO HETEROCYCLIC COMPOUNDS, COMPOSITION CONTAINING SAME AND PROCESS FOR PLANT GROWTH REGULATION USING SAME

[75] Inventors: Mark A. Dekeyser, Waterloo, Canada; Allen R. Blem, Cheshire, Conn.

[73] Assignees: Uniroyal Chemical Company, Inc., Middlebury, Conn.; Uniroyal Chemical Ltd.,/LTEE, Elmira, Canada

[21] Appl. No.: 794,540

[22] Filed: Nov. 19, 1991

Related U.S. Application Data

[62] Division of Ser. No. 590,909, Oct. 1, 1990, Pat. No. 5,070,211.

[51] Int. Cl.$^5$ .............................................. A01N 43/32
[52] U.S. Cl. ............:.................................. 71/76; 71/88
[58] Field of Search ................................ 71/88, 76, 75

Primary Examiner—Richard L. Raymond
Assistant Examiner—B. Bembenizk
Attorney, Agent, or Firm—Glenn E. Karta

[57] ABSTRACT

A compound having the structural formula

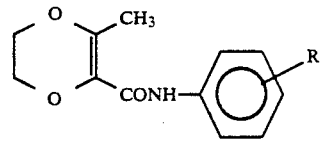

where R is at least one of hydrogen, $C_1$–$C_4$ alkyl, $C_1$–$C_4$ alkoxy, halogen, cyano, phenyl, phenoxy, benzyl or $COOR^1$; and $R^1$ is $C_1$–$C_4$ alkyl is disclosed. A composition comprising a growth regulant effective amount of the compound and a carrier therefor is also set forth. In addition, a process for regulating plant growth comprising applying a plant growth regulant effective amount of the compound to the locus of the plant whose growth is to be regulated is taught.

4 Claims, No Drawings

DIOXO HETEROCYCLIC COMPOUNDS, COMPOSITION CONTAINING SAME AND PROCESS FOR PLANT GROWTH REGULATION USING SAME

This is a division of application Ser. No. 07/590,908 filed Oct. 1, 1990 (now U.S. Pat. No. 5,070,211).

BACKGROUND OF THE DISCLOSURE

1. Field of the Invention

The present invention is directed to a novel class of dioxo heterocyclic carboxamide compounds. More specifically, the instant invention is directed to a class of substituted dioxo heterocyclic carboxamide compounds useful as plant growth regulants.

The importance of plant growth regulants to the economic viability of agriculture continues to grow in importance. This is to be expected in view of the important functions provided by these agricultural chemicals. Plant growth regulants are now for dwarfing, cessation of terminal growth, inhibition of axillary and intercalary growth, increase in plant yield and the like. These applications are not only essential to economic viability, which results from increased production of economically important crops, but, in addition, they are also of increasing utility in the successful production of ornamental plants. It goes without saying that plant growth regulants greatly improve the appearance of ornamental plants, without the requirement of difficult and expensive manual labor.

An important characteristic of plant growth regulants, which excludes many otherwise effective compounds which regulate plant growth, is the requirement that they exhibit low foliar phytotoxicity. That is, an effective plant growth regulant must not only retard vegetative growth and provide the functions discussed above but must also do so without being toxic or in any way have any adverse effect on the plant other than regulating its growth.

Among the more important commercial agricultural plants are wheat and barley. These crops are beneficially affected by control of their growth in that such control optimizes yield of these important grains.

2. Background of the Prior Art

There is a dearth of prior art directed to dioxo heterocyclic compounds substituted with carboxamides. A class of dioxo heterocyclic compounds is identified in Kuznetsov et at., Ukr. Khim. Zh., 42 (10), 1063-1067 (1976). An English abstract of this Russian language article appears in Chemical Abstracts at CA 86 (7):43631z. Kuznetsov et al. discloses 5,6-N-phenyl-2,4-dioxin-2-carboxamide and 5,6-dihydro-N-4-chlorophenyl-1,4-dioxin-2-carboxamide. These compounds are not recited to possess any specific utility and are distinguished from the class of 5,6-dihydro-3-methyl-N-phenyl-1,4-dioxin-2-carboxamide compounds.

BRIEF SUMMARY OF THE INVENTION

A new class of plant growth regulants has been developed which provides excellent plant growth regulation with attendant low foliar phytotoxicity. These admirable properties are particularly noted when this new class of regulants are applied to wheat and barley crops.

In accordance with the present invention a new class of compounds having the structural formula

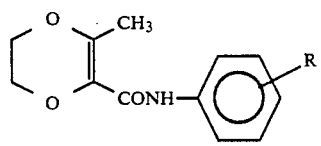

where R is at least one of hydrogen $C_1-C_4$ alkyl, $C_1-C_4$ alkoxy, halogen, cyano, phenyl, phenoxy, benzyl or $COOR^1$; and $R^1$ is $C_1-C_4$ alkyl is provided.

In further accordance with the present invention a composition is disclosed. The composition comprises a plant growth regulant effective amount of the compound having the structural formula I and a carrier therefor.

In still further accordance with the present invention, a process for controlling plant growth is taught. In this process a plant growth regulant effective amount of the compound of the present invention is applied to the locus of the plant whose growth is to be regulated.

DETAILED DESCRIPTION

The compound of the present invention has the structural formula

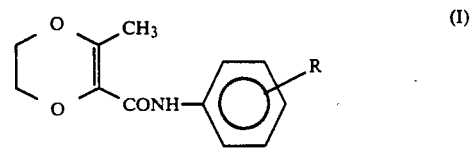

where R is at least one of hydrogen, $C_1-C_4$ alkyl, $C_1-C_4$ alkoxy, halogen, cyano, phenyl, phenoxy, benzyl or $COOR^1$; and $R^1$ is $C_1-C_4$ alkyl.

Preferably, the compound having the structural formula I is characterized by R being at least one of hydrogen, $C_1-C_4$ alkyl, $C_1-C_4$ alkoxy, halogen, cyano, phenyl or phenoxy.

More preferably, the compound having the structural formula I is characterized by R being at least one of hydrogen, methyl, isopropoxy, phenoxy, chlorine or cyano.

Of particular interest are the species wherein the structural formula I is characterized by (1) R being hydrogen; (2) R being methyl in the meta or para position; and (3) wherein R is 2,3-dimethyl.

Compounds having the structural formula I are prepared in a process wherein an acid compound of the formula

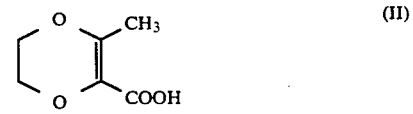

is reacted with thionyl chloride ($SOCl_2$), to produce the intermediate acid chloride having the structural formula

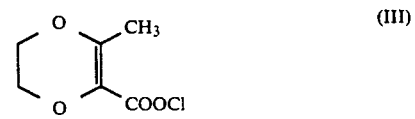

The compound having the structural formula III is, in turn, reacted with an aniline compound having the structural formula

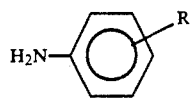 (IV)

where R has the meanings given for the compound having the structural formula I.

In particular, the above process for forming the compounds of the present application involve the reaction of the compound having the structural formula II with thionyl chloride by contacting the two compounds for one to three hours under reflux. The resultant product mixture of this reaction is treated to remove the excess thionyl chloride under reduced pressure resulting in the formation of the intermediate acid chloride having the structural formula III. The acid chloride intermediate is thereafter dissolved in a solvent, preferably ethyl ether, and contacted with the compound having the structural formula IV. The compound having the structural formula IV is usually contacted as a solution, the solvent of which is preferably diethyl ether. Contact of compounds III and IV preferably occurs by the dropwise addition of the aforementioned solution of the aniline compound having the structural formula IV into a solution of the intermediate acid chloride having the structural formula III at a temperature in the range of between about 5° C. and 15° C. The dropwise addition usually occurs over a period of about 1 to 3 hours. The product of this reaction is contacted with water to produce two layers, an organic ether layer and a water layer. The organic ether layer is separated, washed with dilute hydrochloric acid and dried over anhydrous sodium sulfate. The solvent of the resultant solution is evaporated to produce the dioxo heterocyclic carboxamide compound having the structural formula I.

The present invention is also directed to a composition which comprises a plant growth regulant effective amount of the compound having the structural formula I and a carrier therefor. The carrier component of the composition of the present invention may be liquid, solid or a mixture thereof.

In the preferred embodiment wherein a liquid carrier is utilized, the liquid may be a solvent, a dispersant or both. In the case where the liquid carrier is a solvent, the solvent is an organic compound. Organic compounds within the contemplation of the solvent carrier of the composition of the present invention, which may be polar or non-polar, include acetone, methanol, isopropanol, t-butyl alcohol, cyclohexanone, n-butyl alcohol, toluene, xylene, dioxane, dimethylformamide, dimethylsulfoxide, ethylene dichloride and N-methylpyrrolidone.

A second liquid composition, within the contemplation of the present invention, is an emulsion. An emulsion is formed when the compound having the structural formula I is dispersed in water in the presence of a surface active agent. In a preferred embodiment, an emulsion is formed by initially preparing the first preferred liquid composition, a solution of the type discussed immediately above. That solution is then dispersed in water and a surface active agent added thereto to form the emulsion.

Surface active agents suitable for use in forming the emulsion of this invention are known to those skilled in the art. *McCutcheon's Detergents and Emulsifiers*, Allured Publishing Corp., Ridgewood, N.J. (1970); U.S. Pat. No. 2,514,916 and U.S. Pat. No. 2,547,734 provide examples of surface active agents useful in forming emulsions within the contemplation of the composition of the present invention. The above recited references are therefore incorporated herein by reference. As set forth in the above-mentioned references, the surface active agents may be anionic, cationic or non-ionic.

In another preferred embodiment of the liquid composition of the present invention, the composition employs a liquid dispersant as the carrier. In this embodiment, the plant growth regulant, the compound having the structural formula I, is mixed with water in the absence of a surface active agent. The dispersant liquid composition, in an alternate embodiment, is prepared by initially forming a solution of the compound having the structural formula I, as discussed above, and thereafter dispersing the solution in water, again in the absence of a surface active agent.

In still another embodiment of the liquid composition of the subject invention, an aerosol is utilized. An aerosol carrier is liquid under pressure but is a gas under ambient temperature and pressure conditions. Usually, an aerosol formulation is prepared by first preparing a solution of the compound having the structural formula I in a less volatile solvent of the type discussed above. The resultant solution is admixed with the highly volatile liquid aerosol carrier and so applied.

As stated above, the composition of the present invention may also be a solid composition employing a solid carrier. Solid carriers useful in the formation of the plant growth regulant composition of this invention include dusts, granules, wettable powders, pastes and water soluble solids. For example, the plant growth regulant composition of this invention may be applied as a dust when admixed with, adsorbed onto or absorbed onto a powdered solid carrier such as a mineral silicate, e.g., mica, talc, pyrophyllite and clays.

Additional solid compositions can be prepared from granular formulations of the compound having the structural formula I using a granular or pelletized form of carrier such as granular clay, vermiculite, charcoal, corncobs or the like. The use of granular formulations are particularly suitable for application by broadcasting, side dressing, soil incorporation, seed treatment and the like.

The use of both solid and liquid carriers to produce a solid-liquid composition within the contemplation of the present invention is prepared by dispersing a solid, upon which the active compound is absorbed or adsorbed, in a liquid dispersant. Such a composition preferably includes a surface active agent to maintain the solid particles dispersed in the liquid dispersant.

It is emphasized that the plant growth regulant composition of the present invention may utilize a carrier which is itself active. That is, the carrier may be a plant growth regulant, an insecticide, an acaricide, a fungicide, a bactericide or the like.

As stated above, the concentration of the compound having the structural formula I in the composition of this invention is a plant growth regulant effective amount. A plant growth regulant effective amount depends upon such regulated, soil conditions and chemistry, and the climatic conditions under which the plant is grown. Generally, the concentration of compound I, which is representative of a plant growth regulant effective amount in the composition of the present invention, may range from about 0.1% to about 95% by weight. However, when the plant growth regulant is applied in spray dilutions, the concentration may be as low as only a few parts of the active compound, compound I, per million parts of composition. On the other hand, when ultra-low volume applications are utilized, full strength concentrates may be applied.

The present invention is also concerned with a process for regulating plant growth. In this process a plant growth regulant effective amount of the compound having the structural formula I is applied to the locus of the plant whose growth is to be regulated. The definition of a plant growth regulant effective amount in the process of the present invention is as defined above in the discussion of the composition of this invention. That is, the concentration of a plant growth regulant effective amount in equivalent to the plant growth regulant effective amount employed in the process of the subject invention.

The method of application of the active compound, the compound having the structural formula I, in the process of this invention can vary widely. The compound can be directly applied to the plant to be regulated, as, for example, by spraying the plant with a plant growth regulant effective amount of compound I. Alternatively, the plant growth regulant can be applied to the soil. When applied to the soil the plant growth regulant may be applied as a spray. Alternatively, compound I may be applied neat to the soil or as a liquid or solid composition. Independent of the method of application, the application rate of compound I to the soil will usually range from about 0.01 to about 25 lbs. of compound I per acre of foliage. The most suitable rate of application, of course, is a function of such factors as the particular plant growth regulant response desired, soil type, soil pH, soil organic matter content, wind velocity, quantity and intensity of rainfall before and after treatment, air and soil temperature, light intensity and light duration during the period of application. All of these factors, including the delivery composition adjuvants, influence the efficacy of compound I as a plant growth regulant.

The following examples are given to illustrate the scope of the instant invention. Because these examples are given for illustrative purposes only, the scope of the present invention should not be limited thereto.

EXAMPLE 1

Preparation of 5,6-Dihydro-3-methyl-N-phenyl-1,4-dioxin-2-carboxamide (Compound No. 1)

A mixture of 5,6-dihydro-3-methyl-1,4-dioxin-2-carboxylic acid (450 mg.) and thionyl chloride (1.5 g.) was refluxed for 1.5 hours. The product mixture of this contact was subjected to reduced pressure wherein unreacted thionyl chloride was evaporated. The product of this refluxing step, after removal of the unreacted thionyl chloride, the corresponding acid chloride, was dissolved in diethyl ether (20 ml.) at 10° C. To this solution of the acid chloride product was added aniline (700 mg.) dissolved in diethyl ether (20 ml.). The aniline solution was added dropwise. The product of this contact was stirred for two hours. Thereafter, water (50 ml.) was added to the product which resulted in the formation of two phase liquid, a water layer and an organic layer. The water layer was disgarded. The organic layer was washed with dilute hydrochloric acid, dried over anhydrous sodium sulfate followed by evaporation of the ether solvent. The result of these operations was a solid. The solid was washed with hexane and filtered. The solid product of this purification was 5,6-dihydro-3-methyl-N-phenyl-1,4-dioxin-2-carboxamide (650 mg.). This product was characterized by a melting point of 85° C. to 87° C.

EXAMPLE 2

Preparation of Compound Nos. 2 to 14

Additional compounds were prepared in accordance with the procedure of Example 1. These compounds are summarized in Table I below. For convenience, Table I also includes Compound No. 1, the product of Example 1. Each of these compounds, except for Compound Nos. 4 to 6 and 12, are identified in Table I by their melting point. The compounds not identified by their melting points are identified in Table II, which follows Table I, by their nuclear magnetic resonance spectroscopy characteristics. It is noted that of the four compounds identified in Table II three of them were oils at ambient pressure.

TABLE I

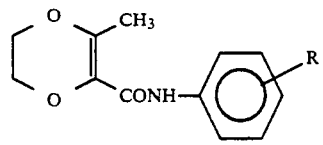

| Cpd. No. | R | Melting Point, °C. |
|---|---|---|
| 1 | H | 85-87 |
| 2 | 2-CH$_3$ | 70-72 |
| 3 | 3-CH$_3$ | 71-73 |
| 4 | 2-C$_6$H$_5$ | oil |
| 5 | 2,3-CH$_3$ | — |
| 6 | 2-CH$_2$C$_6$H$_5$ | oil |
| 7 | 4-OC$_6$H$_5$ | 83-85 |
| 8 | 4-Cl, 3-COOCH(CH$_3$)$_2$ | 103-105 |
| 9 | 2-Cl | 108-111 |
| 10 | 3-CN | 160-163 |
| 11 | 3-OCH(CH$_3$)$_2$ | 79-81 |
| 12 | 2,6-C$_2$H$_5$ | oil |
| 13 | 2-CH(CH$_3$)$_2$ | 79-82 |
| 14 | 4-OCH$_3$ | 59-61 |

TABLE II

| | NUCLEAR MAGNETIC RESONANCE CHARACTERISTICS |
|---|---|
| Cpd. No. | NMR(CDCl$_3$) |
| 4 | s(3)2.3; m(4)4.0; m(9)7.2-7.7; s(1)8.5 |
| 5 | s(3)2.2; s(3)2.3, s(3)2.35; s(4)4.1; m(3) 7.0-7.8; s(1)8.1 |
| 6 | s(3)2.2; m(6)3.8-4.1; m(9)6.8-7.3; s(1)8.1 |
| 12 | t(6)1.2; s(3)2.3; q(4)2.6; s(4)4.1; m(3) 7.1-7.3; s(1)7.7 |

REMARKS:
(1) s = singlet, d = doublet, t = triplet, q = quartet and m = multiplet.
(2) The number in parenthesis represents the number of protons.
(3) CDCl$_3$ is deuterated chloroform.

EXAMPLE 3

Plant Growth Regulation of Barley Plants

Spray emulsion compositions of each of Compound Nos. 1 to 14, characterized by a concentration of 3,000 ppm, were prepared. These emulsions were prepared by dissolving 300 mg. of each of Compound Nos. 1 to 14 in acetone (10 ml.) to which ethoxylated sorbitan monolaurate (30 mg.), an emulsifying agent, was added. An emulsion was formed by the addition of distilled water. The quantity of water added was such that the total volume of the emulsion was 100 ml.

The thus formed emulsions were separately applied to barley plants in 4 inch square plastic pots. Each of the pots contained 8 barley plants, the product of 10 barley seeds sown in greenhouse potting soil (500 g.) which had been thinned out by the removal of excess plants. These compositions were applied as a spray under a pressure of 20 psi for 30 seconds. This spraying resulted in the wetting of the foliage to the drip point.

The so-treated plants were returned to the greenhouse, wherein initial growth occurred, under normal light and water conditions for a one week period. At this point they were compared to untreated check plants which were identically grown but for the absence of spraying with the plant growth regulant compositions. The plants were then scored for percent growth retardation and percent phytotoxicity based on the performance of the check plants. The results of this test appear in Table III.

TABLE III

| Cpd. No. | % Retardation | % Phytotoxicity |
|---|---|---|
| 1 | 45 | 0 |
| 2 | 20 | 10 |
| 3 | 50 | 0 |
| 4 | 0 | 75 |
| 5 | 45 | 0 |
| 6 | 0 | 0 |
| 7 | 0 | 0 |
| 8 | 0 | 0 |
| 9 | 0 | 0 |
| 10 | 0 | 0 |
| 11 | 0 | 5 |
| 12 | 0 | 0 |
| 13 | 0 | 0 |
| 14 | 0 | 0 |

EXAMPLE 4

Plant Growth Regulant Effect of Compound Nos. 1 to 14 on Wheat and Barley

Emulsions of Compound Nos. 1 to 14 were prepared in accordance with the procedure of Example 3. However, the emulsions of this example had a reduced concentration of 1,000 ppm. Each of the emulsions were sprayed on pots containing barley plants. In addition, wheat plants were similarly treated. Again, check plants of wheat and barley were identically prepared but were not subjected to treatment with the plant growth regulant compounds. They were utilized as a test of the effectiveness of the compounds of this invention.

The treated and untreated plants were allowed to grow, after application of Compound Nos. 1 to 14 to the test plants, in a greenhouse under normal light and water conditions for one week. At that point, the height of the check plants were measured. The plants treated with Compound Nos. 1 to 14 were similarly measured and the height of these treated plants, as a percent of the untreated plants, was recorded. These results appear in Table IV.

TABLE IV

| | Growth Retardant Activity at 1,000 ppm. | |
|---|---|---|
| Cpd. No. | Height as % of Check Plants | |
| | Wheat | Barley |
| 1 | 77 | 100 |
| 2 | 75 | 82 |
| 3 | 45 | — |
| 4 | 83 | 100 |
| 5 | 56 | 52 |
| 6 | 97 | 100 |
| 7 | 81 | 79 |
| 8 | 94 | 100 |
| 9 | 69 | 57 |
| 10 | 87 | 76 |
| 11 | 87 | 32 |
| 12 | 98 | 99 |
| 13 | 92 | 97 |
| 14 | 100 | 91 |
| Check | 100 | 100 |

The above embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A composition comprising a) a plant growth regulant effective amount of a compound having the following structure:

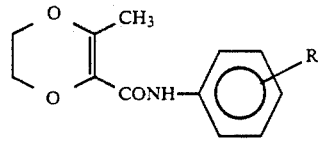

where R is at least one of hydrogen, $C_1$-$C_4$ alkyl, $C_1$-$C_4$ alkoxy, halogen, cyano, phenyl, phenoxy, benzyl or $COOR^1$ with $R^1$ being $C_1$-$C_4$ alkyl; and b) a carrier.

2. A process for controlling plant growth, comprising applying a plant growth regulant amount of a compound having the following structure:

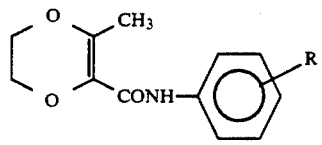

where R is at least one of hydrogen, $C_1$-$C_4$ alkyl, $C_1$-$C_4$ alkoxy, halogen, cyano, phenyl, phenoxy, benzyl or $COOR^1$ with $R^1$ being $C_1$-$C_4$ alkyl; to the locus of the plant whose growth is to be regulated.

3. A process in accordance with claim 2 wherein the plant to be regulated is barley.

4. A process in accordance with claim 2 wherein the plant to be regulated is wheat.

* * * * *